United States Patent
Lucast et al.

(10) Patent No.: US 6,198,016 B1
(45) Date of Patent: Mar. 6, 2001

(54) WET SKIN ADHESIVE ARTICLE

(75) Inventors: Donald H. Lucast, North St. Paul; Donald R. Battles, Arden Hills, both of MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/329,514

(22) Filed: Jun. 10, 1999

Related U.S. Application Data

(60) Provisional application No. 60/110,357, filed on Dec. 1, 1998.

(51) Int. Cl.[7] .......................................... A61F 13/00
(52) U.S. Cl. ................... 602/41; 602/44; 602/47; 602/49; 602/50; 602/54
(58) Field of Search .................. 602/41, 44, 47, 602/49, 50, 54; 424/448, 445

(56) References Cited

U.S. PATENT DOCUMENTS

| | | |
|---|---|---|
| H1565 | 7/1996 | Brodof et al. . |
| 3,825,379 | 7/1974 | Lohkamp et al. . |
| 3,849,241 | 11/1974 | Butin et al. . |
| 3,954,697 | 5/1976 | McConnell et al. . |
| 4,072,812 | 2/1978 | McConnell et al. . |
| 4,379,201 | 4/1983 | Heilmann et al. . |
| 4,429,001 | 1/1984 | Koplin et al. . |
| 4,460,642 | 7/1984 | Errede et al. . |
| 4,554,324 | 11/1985 | Husman et al. . |
| 4,595,001 | 6/1986 | Potter et al. . |
| 4,604,313 | 8/1986 | McFarland et al. . |
| 4,619,979 | 10/1986 | Kotnour et al. . |
| 4,681,579 | 7/1987 | Toussant et al. . |
| 4,684,576 | 8/1987 | Tabor et al. . |
| 4,693,776 | 9/1987 | Krampe et al. . |
| 4,724,114 | 2/1988 | McFarland et al. . |
| 4,737,559 | 4/1988 | Kellen et al. . |
| 4,773,408 | 9/1988 | Cilento et al. . |
| 4,843,134 | 6/1989 | Kotnour et al. . |
| 4,977,892 | 12/1990 | Ewall . |
| 5,064,653 | 11/1991 | Sessions et al. . |
| 5,230,701 | 7/1993 | Meyer et al. . |
| 5,238,733 | 8/1993 | Joseph et al. . |
| 5,369,155 | 11/1994 | Asmus . |
| 5,382,400 | 1/1995 | Pike et al. . |
| 5,451,442 | 9/1995 | Pieniak et al. . |
| 5,451,452 | 9/1995 | Phan et al. . |
| 5,498,478 | 3/1996 | Hansen et al. . |
| 5,506,279 | 4/1996 | Babu et al. . |
| 5,601,851 | 2/1997 | Terakawa . |
| 5,613,942 | 3/1997 | Lucast et al. . |
| 5,637,646 | 6/1997 | Ellis . |
| 5,648,166 | 7/1997 | Dunshee . |
| 5,681,579 | 10/1997 | Freeman . |
| 5,720,832 | 2/1998 | Minto et al. . |
| 5,733,570 | 3/1998 | Chen et al. . |

FOREIGN PATENT DOCUMENTS

| | | |
|---|---|---|
| 091 800 A1 | 10/1982 | (EP) . |
| 0 341 870 | 11/1989 | (EP) . |
| 353 972 A1 | 2/1990 | (EP) . |
| 658 351 B1 | 6/1995 | (EP) . |
| WO 96/07522 | 3/1996 | (WO) . |
| WO 99/27975 | 6/1999 | (WO) . |

OTHER PUBLICATIONS

Wente, Van A., "Superfine Thermoplastic Fibers," *Industrial Engineering Chemistry* 48:1342–1346 (Aug. 1956).

Wente, Van A. et al., "Manufacture of Superfine Organic Fibers," Report No. 4364 of the Naval Research Laboratories, published May 25, 1954.

*Primary Examiner*—Michael A. Brown
*Assistant Examiner*—Lalita M. Hamilton
(74) *Attorney, Agent, or Firm*—Gary L. Griswold; Robert W. Sprague; William J. Bond

(57) ABSTRACT

The present invention provides an adhesive article that includes a backing substrate and a discontinuous adhesive layer disposed thereon, wherein the backing substrate comprises a fibrous web and absorbent particulate material, and further wherein the article has an initial wet skin adhesion of at least 20 g/2.5 cm (0.08 N/cm).

23 Claims, 1 Drawing Sheet

WET SKIN ADHESIVE ARTICLE

CROSS-REFERENCE TO RELATED APPLICATIONS

This application claims the benefit of United States Provisional Patent Application, Ser. No. 60/110,357, filed Dec. 1, 1998, which is incorporated herein by reference.

BACKGROUND OF THE INVENTION

The invention relates to pressure-sensitive adhesive products for use in adhering to skin or like delicate surfaces.

Pressure-sensitive adhesive tapes and the like are used in a wide variety of applications where there is a need to adhere to skin, for example, medical tapes, wound or surgical dressings, athletic tapes, surgical drapes, or tapes or tabs used in adhering medical devices such as sensors, electrodes, ostomy appliances, or the like. A concern with all these adhesive-coated products is the need to balance the objective of providing sufficiently high levels of adhesion to wet skin as well as to dry skin.

One approach in the art to providing pressure-sensitive tapes for application to wet skin has been the use of pattern coated adhesives. A discontinuous adhesive coating on a backing allows the skin to breathe, at least in the areas of the backing not coated with adhesive. This approach is disclosed in U.S. Pat. Nos. 4,595,001 and 5,613,942, as well as EP 353972 and EP 91800. These patent documents generally teach intermittent coating of adhesives onto different backings. For example, U.S. Pat. No. 5,613,942 describes printing pressure-sensitive adhesives using a release coated calender roll process similar to gravure printing. This patent also teaches screen printing. However, pattern coating or printing of adhesives in this manner is problematic as it generally requires solvents, which are environmentally undesirable. Further, residual low molecular weight species can cause skin irritation. It would be preferred from environmental, manufacturing (e.g., elimination of the need for expensive solvent recovery), and performance perspectives to have adhesives coatable directly from a melt phase.

Articles having good wet skin adhesion are described in U.S. Pat. No. 5,613,942. These articles include a porous backing made of non-wettable fibers and a discontinuously coated adhesive. The backing absorbs less than 4% by weight water, thereby allowing water on wet skin to pass through the entire article. Although this provides suitable wet skin adhesion in some applications, there is still a need for articles having good initial wet skin adhesion in other applications, preferably, on the order of the same article's initial dry skin adhesion.

SUMMARY OF THE INVENTION

The present invention provides an adhesive-coated substrate (i.e., an article) comprising a backing substrate and a discontinuous adhesive layer coated (i.e., disposed) thereon, wherein the backing substrate comprises a fibrous web and absorbent particulate material, and further wherein the adhesive-coated substrate has an initial wet skin adhesion of at least about 20 g/2.5 cm (0.08 N/cm). Preferably, the adhesive-coated substrate has an initial dry skin adhesion of at least about 20 g/2.5 cm (0.08 N/cm). More preferably, the initial wet skin adhesion is at least about 65% of the initial dry skin adhesion. Most preferably, the initial wet skin adhesion is about 65% to about 135% of the initial dry skin adhesion.

The adhesive-coated substrate (i.e., adhesive article) can be in the form of a wide variety of articles, such as medical tapes, wound or surgical dressings, athletic tapes, surgical drapes, or tapes or tabs used in adhering medical devices such as sensors, electrodes, ostomy appliances, or the like.

The present invention also provides a method of making an adhesive article. The method includes providing a backing substrate and applying a discontinuous adhesive layer to a major surface thereof, wherein the backing substrate comprises a fibrous web and absorbent particulate material, and further wherein the article has an initial wet skin adhesion of at least 20 g/2.5 cm (0.08 N/cm). The step of applying can occur by laminating the adhesive layer to the backing substrate, spray coating, screen printing, or the like. Thus, "adhesive-coated" as used herein includes, for example, a laminated layer of an adhesive on the backing substrate.

A method of using an adhesive article is also provided. The method includes providing an adhesive article comprising a backing substrate and a discontinuous adhesive layer disposed thereon, wherein the backing substrate comprises a fibrous web and absorbent particulate material, and further wherein the article has an initial wet skin adhesion of at least 20 g/2.5 cm (0.08 N/cm); and adhering the adhesive article to skin.

DESCRIPTION OF THE PREFERRED EMBODIMENTS

Figure 1:
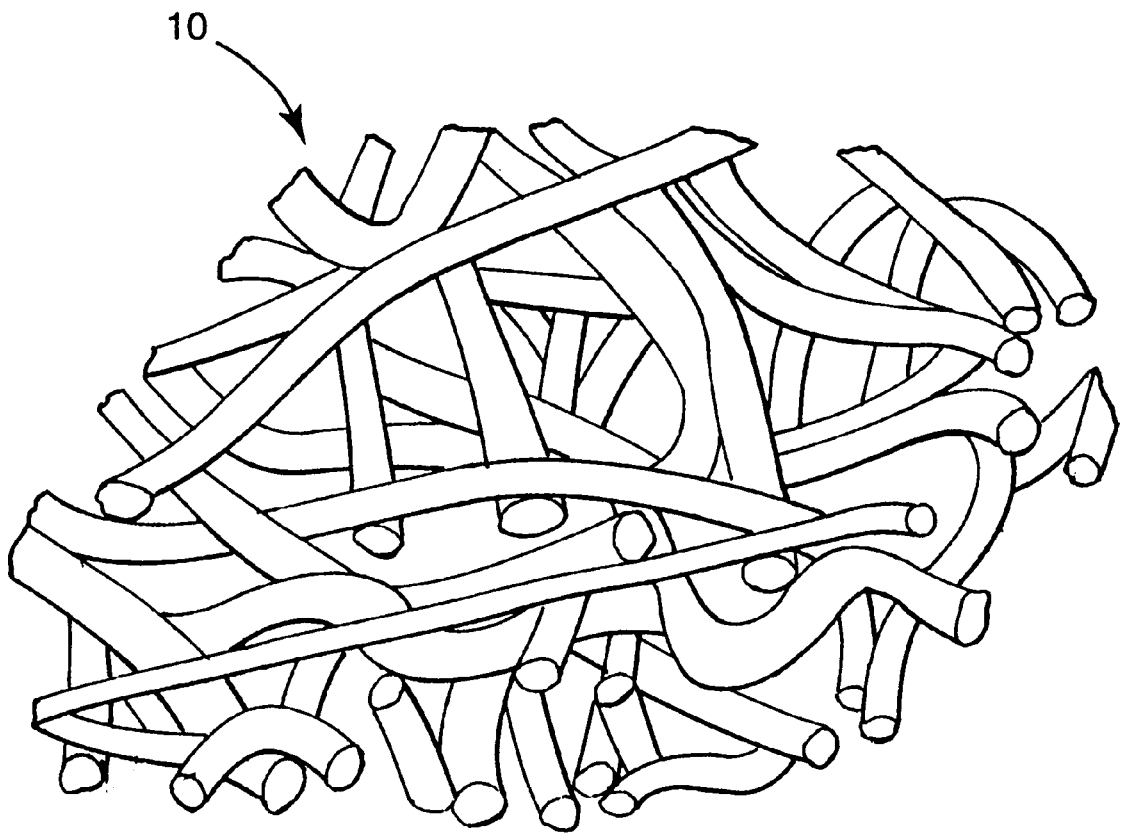
FIG. 1 is a perspective view of the breathable fibrous adhesive nonwoven web used in the invention tape.

The present invention provides articles having an adhesive-coated substrate (i.e., adhesive article) that includes a backing substrate having a discontinuous adhesive layer thereon. The backing substrate includes one or more particle-containing layers of a fibrous material. The particles (i.e., particulate material) enhance the water absorbency, and hence, the wet skin adhesion, of the articles. Preferably, the adhesive article has an initial wet skin adhesion of at least about 20 g/2.5 cm (0.08 N/cm), and more preferably, at least about 40 g/2.5 cm (0.16 N/cm). Preferably, the adhesive article has an initial dry skin adhesion of at least about 20 g/2.5 cm (0.08 N/cm), and more preferably, an initial dry skin adhesion is at least about 40 g/2.5 cm (0.16 N/cm). Preferably, the adhesive article has an initial wet skin adhesion that is at least about 65%, more preferably, at least about 75%, and most preferably, at least about 100%, of the initial dry skin adhesion. Typically, the initial wet skin adhesion will be less than the initial dry skin adhesion; however, it can be higher (e.g., 110% of the initial dry skin adhesion). For certain preferred embodiments, the initial wet skin adhesion is about 65% to about 135% of the initial dry skin adhesion. The comparison of wet to dry skin adhesion can be carried out using the test protocol described in the Examples Section. Herein, wet skin has visually observable water thereon.

A wide variety of materials can be used to form the particle-containing layers. Webs made from natural or synthetic fibers or mixtures thereof can be used. Woven or nonwoven materials can be employed, with nonwoven materials being preferred for most applications. Melt-blown or spunbond techniques can be employed to make such nonwoven webs. Nonwoven webs can also be prepared on a Rando Webber (Rando Corporation, Macedon, N.Y.) airlaying machine or on a carding machine. Further details concerning the backing substrate are discussed below.

The particles preferably are adhered to the fibers in the particle-containing layer. The actual nature of the adhesion will depend on the particles and fibers that are employed and the manner in which the particles are introduced into the web. Adhered particles will desirably exhibit "area contact" with one or more adjacent fibers, that is, they will appear to make more than mere point contact at areas where a fiber may touch a particle. Preferably, at least some of the fibers in the particle-containing layer should exhibit sufficient tackiness when being formed so that they will adhere to each other at room temperature (20–25° C.).

If the backing substrate is in the form of a laminate, additional components could be used, such as absorbent layers for adhesive bandage products, casting material for immobilization devices, or the like. If absorbent layers are used however, they need to be thin, coherent, conformable, and able to flex if used behind the discontinuous adhesive layer. For example, for additional improvement with respect to adhesion to wet skin it is possible that the backing substrate include an absorbent material that does not include particles as described in U.S. patent application Ser. No. 09/201,954, filed on Dec. 1, 1998, entitled "Low Trauma Adhesive Article." There may be one or more additional layers, at least one of which is a breathable, liquid impervious film. Typically this film is the outermost (i.e., top) layer. Examples of film materials include polyurethanes, polyolefins, metallocene polyolefins, polyesters, polyamides, polyetheresters, and A-B block copolymers, such as KRATON copolymers available from Shell Chemical Co. Preferably, the outermost layer is a film that is substantially impervious to fluids, such as could arise from the external environment, yet permit passage of moisture vapor, such that the adhesive-coated substrate (i.e., adhesive article) is breathable (typically, having a moisture vapor transmission rate (MVTR) of at least about 500 $g/m^2/day$).

If absorbent layers that do not contain particles are used, they preferably should not be thick absorbent batts comprised of discontinuous non-coherent fibers such as wood pulp. These thick batts have high levels of absorbency and fluid holding capacity, but this is undesirable for a medical tape where fluid drainage per unit area is very low in an area directly adhered to by a tape product. Preferably, absorbent layers if used in combination with the backing would be in an area of the backing not coated with the adhesive, which area is intended to cover an open wound or the like where there is active liquid drainage.

Backing Substrate

The fibrous backing substrate to which the adhesive is adhered is an air-permeable (i.e., porous) backing such as is provided by a nonwoven web, a woven fabric, or a knitted fabric, for example. The fibers of the backing substrate may be absorbent or nonabsorbent, and typically they are non-water absorptive. The fiber structures useful in the backing substrate of the present invention can include a multilayer configuration, a coated configuration, and a solid homogeneous configuration. Suitable multilayer fibers preferably have cores and outer layers composed of one or more polymers selected from polyolefins, polyesters, polyamides, and polyurethanes. Suitable coated fibers preferably have cores made of these polymers with coatings covalently bonded, embedded, or adhered thereto. The homogeneous fibers preferably are made of any of the polymers listed above. Such fibers can be formed into backings using known weaving, knitting, or nonwoven techniques. Suitable such backing substrates are disclosed, for example, in U.S. Pat. No. 5,613,942.

In preferred embodiments, the particle-containing layer desirably is formed using the apparatus discussed, for example, in Wente, Van A., "Superfine Thermoplastic Fibers", *Industrial Engineering Chemistry*, Vol. 48, pages 1342–1346; Wente, Van A. et al., "Manufacture of Superfine Organic Fibers", Report No. 4364 of the Naval Research Laboratories, published May 25, 1954; and in U.S. Pat. No. 3,825,379 (Lohkamp et al.) and U.S. Pat. No. 3,849,241 (Butin et al.). The microfine fibers described in these references are termed meltblown fibers and are generally substantially continuous and form into a coherent web between the exit die orifice and a collecting surface (the "collector") by entanglement of the microfibers due in part to the turbulent airstream in which the fibers are entrained. When formed by meltblown processes, the individual fibers generally have an effective fiber diameter about 100 microns or less in diameter, more preferably about 50 microns or less in diameter, and most preferably about 25 microns or less in diameter. The particle-containing layer can also be formed by other conventional melt spinning processes, such as spunbond processes. When formed by melt spinning processes, the fibers of the particle-containing layer preferably are about 100 microns or less in diameter.

The fibers in the particle-containing layer can include pressure-sensitive adhesive fibers that will impart durable tackiness to the particle-containing layer. However, fibers that are not durable pressure-sensitive adhesives can also be employed, so long as the fibers are sufficiently tacky for a temporary period after a particle-free web is formed from such fibers on a collector and cooled to room temperature (e.g., for at least about 30 seconds, preferably for at least about two hours, and most preferably for at least about one or more days duration) so that the particles will subsequently adhere to the fibers. For brevity, the pressure-sensitive adhesive fibers and the temporarily tacky fibers will be referred to collectively as "adhesive fibers."

The particle-containing layer may also include non-adhesive fibrous material intimately commingled with the adhesive fibers to provide the layer as a whole with suitable tensile strength, breathability, moldability and other desired properties. The commingled adhesive fibers and non-adhesive fibrous material can be present in separate individual fibers, or as distinct regions in a conjugate fiber, or as part of a blend. For example, conjugate fibers can be in the form of two or more layered fibers, sheath-core fiber arrangements or in "island in the sea" type fiber structures. Generally with any form of multicomponent conjugate fibers, the adhesive fiber component will provide at least a portion of the exposed outer surface of the multicomponent conjugate fiber. Preferably, the individual components of the multicomponent conjugate fibers will be present substantially continuously along the fiber length in discrete zones, which zones preferably extend along the entire length of the fibers.

Conjugate fibers can be formed, for example, as a multilayer fiber as described, for example, in U.S. Pat. No. 5,238,733, U.S. Pat. No. 5,601,851, or International Application No. WO 97/2375. Multilayered and sheath-core melt blown microfibers are described, for example, in the above-mentioned U.S. Pat. No. 5,238,733. The '733 patent describes providing a multicomponent melt blown microfiber web by feeding two separate flow streams of polymer material into a separate splitter or combining manifold. The split or separated flow streams are generally combined immediately prior to the die or die orifice. The separate flow streams are preferably established into melt streams along closely parallel flow paths and combined where they are substantially parallel to each other and the flow path of the resultant combined multilayered flow stream. This multilayered flow stream is then fed into the die or die orifices and through the die orifices. Air slots are disposed on either side of a row of die orifices directing uniform heated air at high velocities at the extruded multicomponent melt streams. The hot high velocity air draws and attenuates the extruded polymeric material which solidifies after traveling a relatively short distance from the die. The high velocity air becomes turbulent between the die and the collector surface causing the melt blown fibers entrained in the airstream mutually to entangle and form a coherent nonwoven web. The particulate materials described in more detail below are fed into the turbulent airstream thereby becoming incorporated into the coherent nonwoven web. This can be done, for example, by using a macrodropper or by other known methods. The resulting solidified or partially solidified particle-containing layer is then formed at the collector by known methods.

Alternatively, conjugate fibers can be formed by a spunbond process such as described in U.S. Pat. No. 5,382,400, where separate polymer flow streams are fed via separate conduits to a spinneret for producing conjugate fibers of a conventional design. Generally, these spinnerets include a housing containing a spin pack with a stack of plates which form a pattern of openings arranged to create flow paths for directing the separate polymer components separately through the spinneret. The spinneret can be arranged to extrude the polymer vertically or horizontally in one or more rows of fibers.

An alternative arrangement for forming melt blown conjugate fibers is described for example, in U.S. Pat. No. 5,601,851. The polymer flow streams are separately fed to each individual die orifice by the use of grooves cut in a distributing and/or separating plate. This arrangement can be used to extrude different polymers from different individual orifices to provide separate distinct fibers which form a coherent entangled web having a substantially uniform distribution of the different fibers. By feeding two separate polymers to an individual die orifice a conjugate fiber can be formed. The apparatus described is suitably used in a melt blowing type arrangement where the die orifices are formed in a row along the die.

The adhesive fibers contain an extrudable pressure-sensitive adhesive material or temporarily tacky material suitable for melt blowing (e.g., a material having an apparent viscosity of from 150 to 800 poise under melt-processing conditions, measured by a capillary rheometer), fiber spinning or spunbond processing. With conjugate fibers or co-formed fibers of different polymers or blends formed from a single die or spinneret, the viscosities of the separate polymer flowstreams should be fairly closely matched for uniform fiber and web formation, but this is not required. In general, matching viscosities will ensure more uniformity in the conjugate fibers by minimizing polymer mixing, which mixing can result in fiber breakage and formation of shot (small particulate polymer material), and lower web tensile properties. However, the presence of discontinuous fibers or shot is not necessarily undesirable as long as the web has the desired overall tensile and cohesive strength.

The particular materials used to form the discrete adhesive fibers, conjugate fibers or blends (of either discrete or conjugate fibers) will depend on the desired application and, in the case of polymer blends or conjugate fibers, upon the chosen non-adhesive fibrous materials. The adhesive fiber material is preferably any hot melt extrudable copolymer or composition having a viscosity in the melt phase suitable for fiber forming by melt processing or in the solution phase for solution spun fibers. Suitable classes of adhesive fiber materials include stretchable block copolymers, polyacrylates, certain polyolefins, and a variety of other tacky or temporarily tacky adhesives. The temporarily tacky adhesives (for example polyalphaolefins, metallocene-catalyzed polyolefins and polyurethanes) provide surprisingly good particle retention.

Stretchable block copolymers. Suitable stretchable block copolymers would include those formed using a tackified elastomer where a preferred elastomer is an A-B type block copolymer wherein the A block and B blocks are configured in linear, radial or star configurations. The A block is formed of a mono-alkenylarene (preferably polystyrene) block having a molecular weight between 4000 and 50,000, and preferably between 7000 and 30,000. The A block content is preferably about 10 to 50 weight percent, and more preferably about 10 to 30 weight percent of the block copolymer. Other suitable A blocks may be formed from alpha-methylstyrene, t-butyl-styrene and other ring-alkylated styrenes, as well as mixtures thereof. The B block is formed of an elastomeric conjugated diene, generally polyisoprene, polybutadiene or copolymers thereof having an average molecular weight from about 5000 to about 500,000, and preferably from about 50,000 to about 200,000. The B block dienes can also be hydrogenated. The B block content is preferably about 90 to 50 percent, and more preferably about 90 to 70 weight percent of the block copolymer.

The tackifying components for the stretchable block copolymers generally are solid tackifying resins, liquid tackifiers, plasticizers or mixtures thereof. Preferably, the tackifying resins are selected from the group of resins at least partially compatible with the polydiene B block portion of the elastomer. Although not preferred, generally a relatively minor amount of the tackifying resin can include resins compatible with the A block, which when present are generally termed end block reinforcing resins. Generally, end block resins are formed from aromatic monomer species. Suitable liquid tackifiers or plasticizers for use in the adhesive polymer include napthenic oils, paraffin oils, aromatic oils, mineral oils or low molecular weight rosin esters, polyterpenes and C-5 resins. Some suitable B-block compatible solid tackifying resins include C-5 resins, resin esters, polyterpenes and the like. The tackified portion of the adhesive generally represents about 20 to 300 parts per 100 parts of the elastomeric phase. Preferably, this is predominately solid tackifier. However, from 0 to 25 weight percent, and preferably from 0 to 10 weight percent of the adhesive composition can be liquid tackifier or plasticizer.

Suitable stretchable block copolymers for melt blown processing are discussed in European Patent No. 0658351, which exemplifies melt-blown fibrous synthetic rubber resin type adhesives used in a disposable absorbent article to immobilize particulate sorbents or used as a pressure-sensitive adhesive attachment (e.g., for a sanitary napkin). Suitable adhesive materials exemplified therein include styrene-isoprene-styrene triblock block copolymers, where the copolymer has coupling efficiencies ranging from 42 to 65 percent (e.g., 58 to 35 percent polystyrene-polyisoprene diblock material would be present), tackified with C-5 hydrocarbon resins (e.g., WINGTACK PLUS and WINGTACK 10 tackifiers from Goodyear) and stabilized with antioxidants. Other commercially available stretchable block copolymers include KRATON block copolymers such as KRATON D1107, KRATON D1112 and KRATON G1657 block copolymers commercially available from Shell Chemical Co., FINAPRENE copolymers commercially available from Fina Oil and Chemical, TAIPOL styrene-butadiene stretchable block copolymers commercially available from Taiwan Synthetic Rubber Corporation, SEPTON SEPS triblock copolymer commercially available from Kuraray Co., and blends (including conjugate fibers) thereof.

Acrylates. Suitable acrylates would include poly (acrylates) derived from (i) at least one monofunctional alkyl (meth)acrylate monomer (i.e., alkyl acrylate or alkyl methacrylate monomer), and (ii) at least one monofunctional free-radically copolymerizable reinforcing monomer. The reinforcing monomer has a homopolymer glass transition temperature ($T_g$) higher than that of the monomer (i) and will increase the glass transition temperature and modulus of the resultant copolymer. Monomers (i) and (ii) are chosen such that a copolymer formed from them is extrudable and capable of forming fibers. Preferably, the monomers used in preparing the adhesive fibers include a monomer (i) that, when homopolymerized, generally has a glass transition temperature of no greater than about 0° C., and a monomer (ii) that, when homopolymerized, generally has a glass transition temperature of at least about 10° C. The glass transition temperatures of monomers (i) and (ii) are typically accurate to within ±5° C. and are measured by differential scanning calorimetry.

Monomer (i) contributes to the flexibility and tack of the copolymer. Preferably monomer (i) has a homopolymer $T_g$ of no greater than about 0° C. Preferably the alkyl group of monomer (i) has an average of about 4 to about 14 carbon atoms. The alkyl group can optionally contain oxygen atoms in the chain thereby forming ethers or alkoxy ethers, for example. Examples of monomer (i) include, but are not limited to, 2-methylbutyl acrylate, isooctyl acrylate, lauryl acrylate, 4-methyl-2-pentyl acrylate, isoamyl acrylate, sec-butyl acrylate, n-butyl acrylate, n-hexyl acrylate, 2-ethylhexyl acrylate, n-octyl acrylate, n-decyl acrylate, isodecyl acrylate, isodecyl methacrylate, and isononyl acrylate. Other examples of monomer (i) include, but are not limited to, poly-ethoxylated or -propoxylated methoxy (meth)acrylate (i.e., poly(ethylene/propylene oxide) mono-(meth)acrylate) macromers (also known as macromolecular monomers), polymethylvinyl ether mono(meth)acrylate macromers, and ethoxylated or propoxylated nonyl-phenol acrylate macromers. The molecular weight of such macromers is typically about 100 to about 600 grams/mole, and preferably, about 300 to about 600 grams/mole. They can perform the function of a crosslinker by forming physical crosslinks that result from the formation of reinforcing domains due to phase separation. Combinations of various monofunctional monomers categorized as monomer (i) can also be used in making the fibers used in the invention.

Reinforcing monomer (ii) increases the glass transition temperature and modulus of the resultant copolymer. Preferably monomer (ii) has a homopolymer $T_g$ of at least about 10° C. More preferably, monomer (ii) is a reinforcing monofunctional (meth)acrylic monomer, including an acrylic acid, a methacrylic acid, an acrylamide, and an acrylate. Examples of monomer (ii) include, but are not limited to, acrylamides, such as acrylamide, methacrylamide, N-methyl acrylamide, N-ethyl acrylamide, N-methylol acrylamide, N-hydroxyethyl acrylamide, diacetone acrylamide, N,N-dimethyl acrylamide, N,N-diethyl acrylamide, N-ethyl-N-aminoethyl acrylamide, N-ethyl-N-hydroxyethyl acrylamide, N,N-dimethylol acrylamide, N,N-dihydroxyethyl acrylamide, t-butyl acrylamide, dimethylaminoethyl acrylamide, N-octyl acrylamide, and 1,1,3,3-tetramethylbutyl acrylamide. Other examples of monomer (ii) include acrylic acid and methacrylic acid, itaconic acid, crotonic acid, maleic acid, fumaric acid, 2,2-(diethoxy)ethyl acrylate, hydroxyethyl acrylate or methacrylate, 2-hydroxypropyl acrylate or methacrylate, methyl methacrylate, isobutyl acrylate, n-butyl methacrylate, isobornyl acrylate, 2-(phenoxy)ethyl acrylate or methacrylate, biphenylyl acrylate, t-butylphenyl acrylate, cyclohexyl acrylate, dimethyladamantyl acrylate, 2-naphthyl acrylate, phenyl acrylate, N-vinyl pyrrolidone, and N-vinyl caprolactam. Combinations of various reinforcing monofunctional monomers categorized as monomer (ii) can also be used to make the adhesive fibers used in the invention.

The acrylate copolymer is preferably formulated to have a resultant $T_g$ of less than about 25° C. and more preferably, less than about 0° C. Such acrylate copolymers preferably include about 60 parts to about 98 parts per hundred (i.e., per one hundred parts total monomer) of at least one alkyl (meth)acrylate monomer (i) and about 2 parts to about 30 parts per hundred of at least one copolymerizable reinforcing monomer (ii). Preferably, the acrylate copolymers have about 85 parts to about 98 parts per hundred of at least one alkyl (meth)acrylate monomer (i) and about 2 parts to about 15 parts of at least one copolymerizable reinforcing monomer (ii).

A crosslinking agent can be used if so desired to build the molecular weight and strength of the copolymer, and hence improve the integrity and shape of the adhesive fibers. Preferably the crosslinking agent is one that is copolymerized with monomers (i) and (ii). The crosslinking agent may produce chemical crosslinks (e.g., covalent bonds). Alternatively, it may produce physical crosslinks that result, for example, from the formation or reinforcing domains due to phase separation or acid base interactions. Suitable crosslinking agents are disclosed in U.S. Pat. Nos. 4,379,201, 4,737,559, 5,506,279, and 4,554,324.

The crosslinking agent is preferably not activated towards crosslinking until after the copolymer is extruded and the fibers are formed. Thus, the crosslinking agent can be a photocrosslinking agent, which, upon exposure to ultraviolet radiation (e.g., radiation having a wavelength of about 250 nanometers to about 400 nanometers), causes the copolymer to crosslink. Preferably, however, the crosslinking agent provides crosslinking, typically, physical crosslinking, without further processing. Physical crosslinking can occur through phase separation of domains which produces thermally reversible crosslinks. Thus, acrylate copolymers prepared from a crosslinker that provides reversible physical crosslinking are particularly advantageous in the preparation of fibers using a melt process.

Preferably, the copolymerizable crosslinking agent is (1) an acrylic crosslinking monomer, or (2) a polymeric crosslinking material having a copolymerizable vinyl group. More preferably, the crosslinking agent is a polymeric crosslinking material having a copolymerizable vinyl group. Preferably, each of these monomers is a free-radically polymerizable crosslinking agent capable of copolymerizing with monomers (i) and (ii). Combinations of various crosslinking agents can be used to make the acrylate copolymer. It should be understood, however, that such crosslinking agents are optional.

The acrylic crosslinking monomer is preferably one that is polymerized with monomers (i) and (ii) and generates free radicals in the polymer backbone upon irradiation of the polymer. An example of such a monomer is an acrylated benzophenone such as described in the above-mentioned U.S. Pat. No. 4,737,559.

Crosslinking polymeric materials (2) that have a copolymerizable vinyl group can preferably be represented by the general formula X-(Y)$_n$-Z wherein X is a copolymerizable vinyl group; Y is a divalent linking group where n can be zero or one; and Z is a monovalent polymeric moiety having a T$_g$ greater than about 20° C. and a weight average molecular weight in the range of about 2,000 to about 30,000 and being essentially unreactive under copolymerization conditions. Particularly preferred vinyl-terminated polymeric monomers (2) useful in making the acrylate copolymers used in the invention may be further defined as having an X group of the formula HR$^1$C=CR$^2$— wherein R$^1$ is a hydrogen atom or a —COOH group and R$^2$ is a hydrogen atom or a methyl group; or a Z group of the formula-{C(R$^3$)(R$^4$)CH$_2$}$_n$—R$^5$ wherein R$^3$ is a hydrogen atom or a lower alkyl group, R$^4$ is a lower alkyl group, n is an integer from 20 to 500, and R$^5$ is a monovalent radical selected from the group consisting of —C$_6$H$_4$R$^6$ and —CO$_2$R$^7$ wherein R$^6$ is a hydrogen atom or a lower alkyl group and R$^7$ is a lower alkyl group.

Such vinyl-terminated polymeric crosslinking monomers are sometimes referred to as macromolecular monomers (i.e., "macromers"). Once polymerized with the (meth) acrylate monomer and the reinforcing monomer, a vinyl-terminated polymeric monomer of this type forms a copolymer having pendant polymeric moieties which tend to reinforce the otherwise soft acrylate backbone, providing a substantial increase in the shear strength of the resultant copolymer adhesive. Specific examples of such crosslinking polymeric materials are disclosed in U.S. Pat. No. 4,554,324.

If used, the copolymerizable crosslinking agent is used in a curatively effective amount, by which is meant an amount that is sufficient to cause crosslinking of the acrylate to provide the desired final adhesion properties in the particle-containing layer. Preferably, if used, the crosslinking agent is used in an amount of about 0.1 part to about 10 parts, based on the total amount of monomers.

If a photocrosslinking agent has been used, the adhesive in the form of fibers can be exposed to ultraviolet radiation having a wavelength of about 250 nm to about 400 nm. The radiant energy in this preferred range of wavelength required to crosslink the adhesive is about 100 milliJoules/square centimeter (mJ/cm$^2$) to about 1,500 mJ/cm$^2$, and more preferably, about 200 mJ/cm$^2$ to about 800 mJ/cm$^2$.

The acrylate copolymers used in the invention can be synthesized by a variety of free-radical polymerization processes, including solution, radiation, bulk, dispersion, emulsion, and suspension polymerization processes. Bulk polymerization methods, such as the continuous free radical polymerization method described in U.S. Pat. Nos. 4,619,979 or 4,843,134, the essentially adiabatic polymerization methods using a batch reactor described in U.S. Pat. No. 5,637,646, and the methods described for polymerizing packaged pre-adhesive compositions described in International Patent Application No. WO 96/07522 may also be utilized to prepare the acrylate polymer from which the adhesive fibers can be prepared. The acrylate copolymers can also be combined with conventional additives such as tackifiers (wood rosin, polyesters, etc.), plasticizers, flow modifiers, neutralizing agents, stabilizers, antioxidants, fillers, colorants, and the like, as long as they do not interfere in the fiber-forming melt process. Initiators that are not copolymerizable with the monomers used to prepare the acrylate copolymer can also be used to enhance the rate of polymerization and/or crosslinking. These additives are incorporated in amounts that do not materially adversely affect the desired properties of the acrylate copolymers or their fiber-forming properties. Typically, they can be mixed into these systems in amounts of about 0.05 volume percent to about 25 volume percent of the adhesive composition.

Polyolefins. Suitable polyolefins would include tackified higher polyolefin elastomer adhesives (e.g., polybutylene adhesives), atactic or substantially atactic polypropylene, and amorphous polyalphaolefin polymers suitable for forming hot melt pressure-sensitive adhesives with or without added tackifier. Polyalphaolefins are preferred. Suitable polyalphaolefins are generally copolymers of a C$_3$ to C$_5$ linear alpha-olefin(s) and a higher (generally C$_6$ to C$_{10}$) alpha-olefin(s). Preferred are copolymers of polyolefins with polyhexene, polyheptene, polyoctene, polynonene and/or polydecene. Preferred polyalphaolefins are described in U.S. Pat. Nos. 3,954,697, 4,072,812 and 4,684,576 where the amorphous polyalphaolefin copolymers can be used without added tackifiers directly to form a pressure-sensitive adhesive. These amorphous copolymers generally have from about 40 mole percent to about 60 mole percent of the higher alpha olefin comonomer(s). However, suitable compatible tackifying resins and plasticizing oils can be used which generally correspond to those used to tackify the synthetic AB block copolymer elastomers described above. For example, suitable compatible liquid or solid tackifiers would include hydrocarbon resins, such as polyterpenes, C-5 hydrocarbon resins, or polyisoprenes. Resin esters of aromatic or aliphatic acids would be suitable. If these tackifiers are used in sufficient amounts, the higher alpha olefin content can be as low as 15 mole percent and still provide suitable adhesive fibers.

Representative commercially-available polyolefins include ASPUN 6805 and ASPUN 6806 ethylene/octene copolymer, both available from Dow Chemical Co., ENGAGE 8400 ethylene/octene copolymer available from DuPont, Dow Elastomers, EXACT 4023 metallocene-catalyzed ethylene/butylene copolymer available from Exxon Chemical Co., REXENE D100, EASTOFLEX D127, and EASTOFLEX E1200 polyalphaolefins, both available from Eastman Chemical Co., VESTOPLAST V520 and VESTOPLAST V750 polyalphaolefin, both available from Hüls America Inc., and blends (including conjugate fibers) thereof.

Other Tacky or Temporarily Tacky Fibrous Materials. Other tacky or temporarily tacky adhesive materials for use in forming the particle-containing layer include polyurethanes such as MORTHANE 440 and MORTHANE 455 polyester-based polyurethanes, both available from Morton International, PELLETHANE polyester-based polyurethanes such as PELLETHANE 2355-85ABR polyurethane available from Dow Chemical Co., ESTANE polyurethanes such as ESTANE 58238 and ESTANE 58661 polyester-based polyurethanes, both available from B.F. Goodrich Specialty Plastics, polydiorganosiloxane polyurea copolymers of the type disclosed in copending U.S. patent application Ser. No. 08/980,925 filed Dec. 1, 1997, and blends (including conjugate fibers) thereof.

Non-Adhesive Fibrous Material. As mentioned above, the particle-containing layer can include non-adhesive fibrous material, as separate individual fibers, or as distinct regions in a conjugate fiber, or as part of a blend. Suitable non-adhesive fibrous materials include lower polyolefins such as polyethylene and isotactic polypropylene, polyesters, polyamides, polystyrenes, and non-tacky polyurethanes.

The non-adhesive fibrous material generally represents from 0 to about 90 percent of the basis weight of the fibers in the particle-containing layer, more preferably about 60 percent to about 80 percent. When the non-adhesive fibrous material is present as a discrete fiber, the fibers are generally intimately commingled with the adhesive fibers. Such commingled fibers can be formed from the die described in U.S. Pat. No. 5,601,851 or in a separate die which could direct the non-adhesive fibrous material directly, or subsequently, into the fiber stream containing the adhesive fibers prior to formation of the commingled fiber web on the collector. The use of multiple dies for forming other types of commingled fibers is known in the art.

Generally, depending on the fiber formation process, suitable antioxidants and heat stabilizers could be used in the present invention to prevent the degradation of the particle-containing layer during the fiber forming process or in use. Also, other conventional additives could be used such as UV absorbents, pigments, particulates, staple fibers, or the like.

Absorbent Particles

The wet skin adhesion characteristics of the present invention are typically provided by an absorbent particulate material, typically in the form of a powder or larger particles (including fibers), herein referred to generally as particulate material or particles. Such particles typically have a length to width ratio (aspect ratio) of no more than about 20:1, and preferably, no more than about 10:1, whereas the aspect ratio for fibers used herein (whether as a structural component of the backing or as an absorbent particle) is typically greater than about 20:1, and preferably, greater than about 100:1. The particles can be of any desired shape, such as round, flake-like, elongated, or irregular, for example. Suitable particles have a particle size (i.e., the longest dimension, which is typically the diameter of a spherical particle) of less than about 800 micrometers (microns).

The particulate material can be distributed uniformly throughout the fibrous web of the backing substrate or can be coated onto either major surface of the web. A sufficient amount of absorbent particulate material is present in or on the web in the backing substrate to provide the desired levels of wet skin adhesion as described above.

The particulate material is sufficiently water absorptive to provide articles having sufficient wet skin adhesion, preferably, at least about 20 g/2.5 cm (0.08 N/cm). Preferably, the particulate material is superabsorbent. Suitable superabsorbent particles are made from polymers that are capable of absorbing at least about 50 times their weight of water. Suitable superabsorbent particulate material can be prepared from carboxymethylcellulose and its sodium and potassium salts, hydroxymethylcellulose, hydroxyethylcellulose, poly(acrylamide), poly(acrylic acid) and its sodium and potassium salts, alginates, and starch-graft copolymers such as those of acrylates and acrylamides and their salts. Examples of such materials are disclosed in U.S. Pat. No. 5,064,653. Although superabsorbent particles are preferred, other absorbent particles can be used if desired, such as gelatins, polysaccharides, gums including pectin, guar gum, xantham gum, and karaya gum.

Particulate material can be incorporated into the web by dropping it into the freshly blown stream of meltblown fibers after the fibers exit from the die and before they reach the collector, using the general procedure described in U.S. Pat. No. 4,429,001.

Additives can be incorporated into the fibrous web of the backing substrate as long as they do not interfere in the fiber-forming melt process or do not detrimentally effect the function and functionality of the final polymer product. Examples of such additives include odor absorbers such as activated carbon, medicaments such as chlorhexidine gluconate, biologically active agents, cosmetic agents, and the like, which can be in particulate form or incorporated into encapsulating agents.

Pressure-Sensitive Adhesive Layer

The articles (i.e., adhesive-coated substrates) of the present invention include a discontinuous layer of an adhesive. This may result from screen printing, melt-spraying, stripe-coating, or laminating processes, or the use of microspheres, for example. Typically, the pressure-sensitive adhesive can be applied to the backing substrate as a pattern by techniques known in the art, such as spray application, roller printing, screen printing, etc.

The pressure-sensitive adhesive used in the articles of the present invention is preferably composed of a water insoluble and nonabsorbent, preferably viscoelastic polymer composition. The pressure-sensitive adhesive is also water tolerant, i.e., it continues to function as an adhesive even in the presence of large amounts of water. Suitable pressure-sensitive adhesives include viscoelastic polymers such as polyacrylates, polyolefins, polyethers, polyisoprenes, butyl rubbers, natural rubbers, styrene-butadiene rubbers, polyurethanes, polyesters, and the like. The viscoelastic polymer can be mixtures or blends of these polymers. Other suitable pressure-sensitive adhesives and methods of applying them in discontinuous layers are described in U.S. Pat. No. 5,613,942.

A preferred discontinuous adhesive layer includes coherent pressure-sensitive adhesive fibers which are intimately entangled each with the other in the form of a coherent breathable fibrous adhesive nonwoven web, attached to a backing substrate. Suitable pressure-sensitive adhesive fiber webs 10 as shown in FIG. 1 can be formed as melt blown microfiber webs using the apparatus discussed, for example, in Wente, Van A., "Superfine Thermoplastic Fibers", *Industrial Engineering Chemistry*, Vol. 48, pages 1342–1346, Wente, Van A. et al., "Manufacture of Superfine Organic Fibers", Report No. 4364 of the Naval Research Laboratories, published May 25, 1954, and in U.S. Pat. Nos. 3,849,241 and 3,825,379, and others. These microfine fibers are termed melt blown fibers and are generally substantially continuous and form into a coherent web between the exit die orifice and a collecting surface by entanglement of the microfibers due in part to the turbulent airstream in which the fibers are entrained. Further, suitable pressure-sensitive adhesive fibers used in the invention adhesive-coated substrate can be formed by other conventional melt spinning processes, such as spunbond processes where the fibers are collected in a web form immediately upon formation. Generally, the adhesive fibers are 100 microns or less in diameter when formed by melt spinning type processes, preferably 50 microns or less.

The discontinuous adhesive layer can also comprise non-pressure-sensitive adhesive fibrous material intimately commingled with the pressure-sensitive adhesive fibers. The commingled pressure-sensitive adhesive fibers or microfibers and non-pressure-sensitive adhesive fibrous material can be present in separate individual fibers or the pressure-sensitive adhesive fibers or microfibers and the non-pressure-sensitive material can form distinct regions in a conjugate fiber and/or be part of a blend. For example, conjugate fibers can be in the form of two or more layered fibers, sheath-core fiber arrangements or in "island in the sea" type fiber structures. In this case, one component layer would comprise the pressure-sensitive adhesive fiber or microfiber and a second component layer would comprise the non-pressure-sensitive adhesive fibrous material. Generally with any form of multicomponent conjugate fibers, the pressure-sensitive adhesive fiber component will provide at least a portion of the exposed outer surface of the multicomponent conjugate fiber. Preferably, the individual components of the multicomponent conjugate fibers will be present substantially continuously along the fiber length in discrete zones, which zones preferably extend along the entire length of the fibers. The individual fibers generally are of a fiber diameter of less than 100 microns, preferably less than 50 microns or 25 microns for microfibers.

Conjugate fibers can be formed, for example, as a multilayer fiber as described, for example, in U.S. Pat. Nos. 5,238,733 and 5,601,851, or PCT Publication WO 97/2375. Multilayered and sheath-core melt blown microfibers are described, for example, in U.S. Pat. No. 5,238,733. Alternatively, conjugate fibers can be formed by a spunbond process such as described in U.S. Pat. No. 5,382,400. An alternative arrangement for forming melt blown conjugate fibers is described for example, in U.S. Pat. No. 5,601,851. These fibers and processes of their manufacture are described in greater detail above with respect to the fibers of the backing substrate. The pressure-sensitive adhesive component comprises an extrudable pressure-sensitive adhesive suitable for melt blowing (generally this requires the adhesive to have an apparent viscosity of from 150 poise to 800 poise, under melt-processing conditions measured by a capillary rheometer) or other fiber spinning processes such as spunbond processing. As discussed above for the fibers of the backing substrate, with conjugate fibers or co-formed fibers of different polymers or blends formed from a single die or spinneret, the viscosities of the separate polymer flowstreams should be fairly closely matched for uniform fiber and web formation, but this is not required. Generally matching viscosities will ensure more uniformity in the conjugate fibers formed in terms of minimizing polymer mixing, which mixing can result in fiber breakage and formation of shot (small particulate polymer material), and lower web tensile properties. However, the presence of discontinuous fibers or shot is not necessarily undesirable as long as the adhesive article has the desired overall adhesive strength.

The particular pressure-sensitive adhesive used in forming discrete pressure-sensitive adhesive fibers, conjugate fibers or blends (in either discrete or conjugate fibers) depends on the adhesive formulation in view of the desired adhesion level as taught in the invention examples and the non-pressure-sensitive adhesive material polymers selected in the case of polymer blends or conjugate fibers. The pressure-sensitive adhesive selected is generally any hot melt extrudable copolymer or composition having a viscosity in the melt phase suitable for fiber forming by melt processing. Suitable classes of pressure-sensitive adhesives include acrylate adhesives, polyalphaolefin adhesives, rubber resin adhesives or the like. Suitable rubber resin adhesives would include those formed using a tackified elastomer where a preferred elastomer is an A-B type block copolymer wherein the A blocks and B blocks are configured in linear (e.g. diblock or triblock copolymer), radial or star configurations. The A block is formed of a mono-alkenylarene, preferably a polystyrene block having a molecular weight between 4000 and 50,000, preferably between 7000 and 30,000. The A block content is preferably about 10 to 50 weight percent, preferably about 10 to 30 weight percent of the block copolymer. Other suitable A blocks may be formed from alpha-methylstyrene, t-butyl-styrene and other ring alkylated styrenes, as well as mixtures thereof. The B block is formed of an elastomeric conjugated diene, generally polyisoprene, polybutadiene or copolymers thereof having an average molecular weight from about 5000 to about 500,000, preferably from about 50,000 to about 200,000. The B block dienes can also be hydrogenated. The B block content is generally 90 percent to 50 percent, preferably 90 percent to 70 percent by weight. The tackifying components for the elastomer-based adhesives generally comprise solid tackifying resin and/or a liquid tackifier or plasticizer. Preferably, the tackifying resins are selected from the group of resins at least partially compatible with the polydiene B block portion of the elastomer. Although not preferred, generally a relatively minor amount of the tackifying resin can include resins compatible with the A block, which when present are generally termed end block reinforcing resins. Generally, end block resins are formed from aromatic monomer species. Suitable liquid tackifiers or plasticizers for use in the adhesive composition include napthenic oils, paraffin oils, aromatic oils, mineral oils or low molecular weight rosin esters, polyterpenes and C-5 resins. Some suitable B-block compatible solid tackifying resins include C-5 resins, resin esters, polyterpenes and the like.

The tackifier portion of the pressure-sensitive adhesive generally comprises from 20 parts to 300 parts per 100 parts of the elastomer phase. Preferably, this is predominately solid tackifier, however, from 0 to 25 weight percent, preferably 0 to 10 weight percent of the adhesive composition can be liquid tackifier and/or plasticizer.

Suitable rubber resin adhesives for melt blown processing are discussed in EP 658,351 which exemplifies melt-blown fibrous synthetic rubber resin type adhesives used in a disposable absorbent article to either immobilize particulate sorbents or used as a pressure-sensitive adhesive attachment (e.g., for a sanitary napkin). Suitable adhesives exemplified are styrene-isoprene-styrene triblock block copolymer based, where the copolymer has coupling efficiencies ranging from 42 to 65 percent (e.g., 58 to 35 percent polystyrene-polyisoprene diblock material would be present), tackified with C-5 hydrocarbon resins (WINGTACK PLUS and WINGTACK 10 available from Goodyear) and stabilized with antioxidants.

Generally, depending on the fiber formation process, suitable antioxidants and heat stabilizers could be used in the present invention to prevent the degradation of the adhesive during the fiber forming process or in use. Also, other conventional additives could be used such as UV absorbents, pigments, particulates, staple fibers or the like.

Suitable poly(acrylate) adhesives are derived from: (A) at least one monofunctional alkyl (meth)acrylate monomer (i.e., alkyl acrylate and alkyl methacrylate monomer); and (B) at least one monofunctional free-radically copolymerizable reinforcing monomer. The reinforcing monomer has a homopolymer glass transition temperature ($T_g$) higher than that of the alkyl (meth)acrylate monomer and is one that increases the glass transition temperature and modulus of the resultant copolymer. Monomers A and B are chosen such that a copolymer formed from them is extrudable and capable of forming fibers. Herein, "copolymer" refers to polymers containing two or more different monomers, including terpolymers, tetrapolymers, etc.

Preferably, the monomers used in preparing the pressure-sensitive adhesive copolymer fibers of the present invention include: (A) a monofunctional alkyl (meth)acrylate monomer that, when homopolymerized, generally has a glass transition temperature of no greater than about 0° C.; and (B) a monofunctional free-radically copolymerizable reinforcing monomer that, when homopolymerized, generally has a glass transition temperature of at least about 10° C. The glass transition temperatures of the homopolymers of monomers A and B are typically accurate to within ±5° C. and are measured by differential scanning calorimetry.

Monomer A, which is a monofunctional alkyl acrylate or methacrylate (i.e., (meth)acrylic acid ester), contributes to the flexibility and tack of the copolymer. Preferably, monomer A has a homopolymer $T_g$ of no greater than about 0° C. Preferably, the alkyl group of the (meth)acrylate has an average of about 4 to about 20 carbon atoms, and more preferably, an average of about 4 to about 14 carbon atoms. The alkyl group can optionally contain oxygen atoms in the chain thereby forming ethers or alkoxy ethers, for example. Examples of monomer A include, but are not limited to, 2-methylbutyl acrylate, isooctyl acrylate, lauryl acrylate, 4-methyl-2-pentyl acrylate, isoamyl acrylate, sec-butyl acrylate, n-butyl acrylate, n-hexyl acrylate, 2-ethylhexyl acrylate, n-octyl acrylate, n-decyl acrylate, isodecyl acrylate, isodecyl methacrylate, and isononyl acrylate. Other examples include, but are not limited to, poly-ethoxylated or -propoxylated methoxy (meth)acrylate (i.e., poly(ethylene/propylene oxide) mono-(meth)acrylate) macromers (i.e., macromolecular monomers), polymethylvinyl ether mono (meth)acrylate macromers, and ethoxylated or propoxylated nonyl-phenol acrylate macromers. The molecular weight of such macromers is typically about 100 grams/mole to about 600 grams/mole, and preferably, about 300 grams/mole to about 600 grams/mole. Combinations of various monofunctional monomers categorized as an A monomer can be used to make the copolymer used in making the fibers of the present invention.

Monomer B, which is a monofunctional free-radically copolymerizable reinforcing monomer; increases the glass transition temperature of the copolymer. As used herein, "reinforcing" monomers are those that increase the modulus of the adhesive, and thereby its strength. Preferably, monomer B has a homopolymer $T_g$ of at least about 10° C. More preferably, monomer B is a reinforcing monofunctional (meth)acrylic monomer, including an acrylic acid, a methacrylic acid, an acrylamide, and an acrylate. Examples of monomer B include, but are not limited to, acrylamides, such as acrylamide, methacrylamide, N-methyl acrylamide, N-ethyl acrylamide, N-methylol acrylamide, N-hydroxyethyl acrylamide, diacetone acrylamide, N,N-dimethyl acrylamide, N,N-diethyl acrylamide, N-ethyl-N-aminoethyl acrylamide, N-ethyl-N-hydroxyethyl acrylamide, N,N-dimethylol acrylamide, N,N-dihydroxyethyl acrylamide, t-butyl acrylamide, dimethylaminoethyl acrylamide, N-octyl acrylamide, and 1,1,3,3-tetramethylbutyl acrylamide. Other examples of monomer B include acrylic acid and methacrylic acid, itaconic acid, crotonic acid, maleic acid, fumaric acid, 2,2-(diethoxy)ethyl acrylate, hydroxyethyl acrylate or methacrylate, 2-hydroxypropyl acrylate or methacrylate, methyl methacrylate, isobutyl acrylate, n-butyl methacrylate, isobornyl acrylate, 2-(phenoxy)ethyl acrylate or methacrylate, biphenylyl acrylate, t-butylphenyl acrylate, cyclohexyl acrylate, dimethyladamantyl acrylate, 2-naphthyl acrylate, phenyl acrylate, N-vinyl pyrrolidone, and N-vinyl caprolactam. Combinations of various reinforcing monofunctional monomers categorized as a B monomer can be used to make the copolymer used in making the fibers of the present invention.

The acrylate copolymer is preferably formulated to have a resultant $T_g$ of less than about 25° C. and more preferably, less than about 0° C. Such acrylate copolymers preferably include about 60 parts to about 98 parts per hundred (i.e., per one hundred parts of total monomer) of at least one alkyl (meth)acrylate monomer and about 2 parts to about 40 parts per hundred of at least one copolymerizable reinforcing monomer. Preferably, the acrylate copolymers have about 85 parts to about 98 parts per hundred or at least one alkyl (meth)acrylate monomer and about 2 parts to about 15 parts of at least one copolymerizable reinforcing monomer.

A crosslinking agent can be used if so desired to build the molecular weight and the strength of the copolymer, and hence improve the integrity and shape of the fibers. Preferably, the crosslinking agent is one that is copolymerized with monomers A and B. The crosslinking agent may produce chemical crosslinks (e.g., covalent bonds). Alternatively, it may produce physical crosslinks that result, for example, from the formation of reinforcing domains due to phase separation or acid base interactions. Suitable crosslinking agents are disclosed in U.S. Pat. Nos. 4,379,201, 4,737,559, 5,506,279, and 4,554,324.

This crosslinking agent is preferably not activated towards crosslinking until after the copolymer is extruded and the fibers are formed. Thus, the crosslinking agent can be a photocrosslinking agent, which, upon exposure to ultraviolet radiation (e.g., radiation having a wavelength of about 250 nanometers to about 400 nanometers), causes the copolymer to crosslink. Preferably, however, the crosslinking agent provides crosslinking, typically, physical crosslinking, without further processing. Physical crosslinking can occur through phase separation of domains which produces thermally reversible crosslinks. Thus, acrylate copolymers prepared from a crosslinker that provides reversible physical crosslinking are particularly advantageous in the preparation of fibers using a melt process.

Preferably, the crosslinking agent is (1) an acrylic crosslinking monomer, or (2) a polymeric crosslinking material having a copolymerizable vinyl group. More preferably the crosslinking agent is a polymeric material having a copolymerizable vinyl group. Preferably, each of these monomers is a free-radically polymerizable crosslinking agent capable of copolymerizing with monomers A and B. Combinations of various crosslinking agents can be used to make the copolymer used in making the fibers of the present invention. It should be understood, however, that such crosslinking agents are optional.

The acrylic crosslinking monomer is preferably one that is copolymerized with monomers A and B and generates free radicals in the polymer backbone upon irradiation of the polymer. An example of such a monomer is an acrylated benzophenone as described in U.S. Pat. No. 4,737,559.

The polymeric crosslinking materials that have a copolymerizable vinyl group is preferably represented by the general formula X-(Y)$_n$-Z wherein: X is a copolymerizable vinyl group; Y is a divalent linking group where n can be zero or one; and Z is a monovalent polymeric moiety having a $T_g$ greater than about 20° C. and a weight average molecular weight in the range of about 2,000 to about 30,000 and being essentially unreactive under copolymerization conditions. Particularly preferred vinyl-terminated polymeric monomers useful in making the microfibers of the present invention are further defined as having: an X group which has the formula HR$^1$C=CR$^2$— wherein R$^1$ is a hydrogen atom or a COOH group and R$^2$ is a hydrogen atom or a methyl group; a Z group which has the formula —{C(R$^3$)(R$^4$)—CH$_2$}$_n$—R$^5$ wherein R$^3$ is a hydrogen atom or a lower (i.e., C$_1$–C$_4$) alkyl group, R$^5$ is a lower alkyl group, n is an integer from 20 to 500, and R$^4$ is a monovalent radical selected from the group consisting of —C$_6$H$_4$R$^6$ and —CO$_2$R$^7$ wherein R$^6$ is a hydrogen atom or a lower alkyl group and R$^7$ is a lower alkyl group.

Such vinyl-terminated polymeric crosslinking monomers are sometimes referred to as macromolecular monomers (i.e., "macromers"). Once polymerized with the (meth)acrylate monomer and the reinforcing monomer, a vinyl-terminated polymeric monomer of this type forms a copolymer having pendant polymeric moieties which tend to reinforce the otherwise soft acrylate backbone, providing a substantial increase in the shear strength of the resultant copolymer adhesive. Specific examples of such crosslinking polymeric materials are disclosed in U.S. Pat. No. 4,554,324.

If used, the crosslinking agent is used in an effective amount, by which is meant an amount that is sufficient to cause crosslinking of the pressure-sensitive adhesive to provide the desired final adhesion properties to the substrate of interest. Preferably, if used, the crosslinking agent is used in an amount of about 0.1 part to about 10 parts, based on the total amount of monomers.

If a photocrosslinking agent has been used, the adhesive in the form of fibers can be exposed to ultraviolet radiation having a wavelength of about 250 nm to about 400 nm. The radiant energy in this preferred range of wavelength required to crosslink the adhesive is about 100 milliJoules/centimeter$^2$ (mJ/cm$^2$) to about 1,500 mJ/cm$^2$, and more preferably, about 200 mJ/cm$^2$ to about 800 mJ/cm$^2$.

The acrylate pressure-sensitive adhesives of the present invention can be synthesized by a variety of free-radical polymerization processes, including solution, radiation, bulk, dispersion, emulsion, and suspension polymerization processes. Bulk polymerization methods, such as the continuous free radical polymerization method described in U.S. Pat. Nos. 4,619,979 or 4,843,134, the essentially adiabatic polymerization methods using a batch reactor described in U.S. Pat. No. 5,637,646, and the methods described for polymerizing packaged pre-adhesive compositions described in International Patent Application No. WO 96/07522, may also be utilized to prepare the polymer used in the preparation of the fibers of the present invention.

The acrylate pressure-sensitive adhesive of the present invention can include conventional additives such as tackifiers (wood rosin, polyesters, etc.), plasticizers, flow modifiers, neutralizing agents, stabilizers, antioxidants, fillers, colorants, and the like, as long as they do not interfere in the fiber-forming melt process. Initiators that are not copolymerizable with the monomers used to prepare the acrylate copolymer can also be used to enhance the rate of polymerization and/or crosslinking. These additives are incorporated in amounts that do not materially adversely affect the desired properties of the pressure-sensitive adhesives or their fiber-forming properties. Typically, they can be mixed into these systems in amounts of about 0.05 weight percent to about 25 weight percent, based on the total weight of the composition.

Suitable polyolefin adhesives would include tackified polyolefin elastomer type adhesives, or amorphous polyalphaolefin polymers suitable for forming hot melt pressure-sensitive adhesives with or without added tackifier. Such amorphous polyalphaolefins are generally copolymers of a $C_3$ to $C_5$ linear alpha-olefin(s) and a higher alpha-olefin(s) (generally $C_6$ to $C_{10}$). Preferred are copolymers of polyolefins with polyhexene, polyheptene, polyoctene, polynonene and/or polydecene. Such amorphous polyalphaolefins are described in U.S. Pat. Nos. 4,264,576, 3,954,697, and 4,072,812 where the amorphous polyalphaolefin copolymers can be used without added tackifiers to directly form a pressure-sensitive adhesive. These amorphous copolymers generally have from 40 to 60 mole percent of the higher alphaolefin comonomer(s). However, suitable compatible tackifying resins and plasticizing oils can be used which generally correspond to those used to tackify the synthetic AB block copolymer elastomers described above. For example, suitable compatible liquid or solid tackifiers would include hydrocarbon resins, such as polyterpenes, C-5 hydrocarbon resins, or polyisoprenes, also resin esters of aromatic or aliphatic acids would be suitable. If these tackifiers are used in sufficient amounts, the higher alphaolefin content can be as low as 15 mole percent and still suitable pressure-sensitive adhesives can be formed.

Suitable non-adhesive materials for use in forming conjugate fibers, for use in blends with the pressure-sensitive adhesive or for use as separate fibers, include polyolefins, polyesters, polyalkylenes, polyamides, polystyrenes, polyarylsulfones, polydienes or polyurethanes; these materials are preferably extensible or slightly elastomeric, but could be elastomeric. Preferred are extensible or slightly elastomeric polyolefins such as polyethylenes, polypropylenes, ethylene-propylene copolymers, ethylene/vinyl acetate copolymers, or metallocene-type polyethylenes having a density of greater than 0.87 grams/cm$^3$. Suitable elastomeric materials would include metallocene-type polyethylene copolymers (apparent density less than 0.87 grams/cm$^3$); polyurethanes (e.g., MORTHANE); polyolefin elastomers (e.g., ethylene/propylene/diene elastomers); A-B block copolymers, as described above, having A blocks formed of poly (vinyl arenes) such as polystyrene and B blocks formed of conjugated dienes such as isoprene, butadiene, or hydrogenated versions thereof (e.g., KRATON elastomers available from Shell Chemical Co.); polyetheresters (such as ARNITAL, available from Akzo Plastics Co.); or polyether block amides (such as PEBAX, available from Atochem Co.). Blends of elastomers, blends of nonelastomers or blends of both elastomers and nonelastomers can also be used for the non-pressure-sensitive adhesive fibers, conjugate fibers or in suitable blend fibers.

The non-pressure-sensitive adhesive material in fibrous form generally comprises 0 to 50 percent of the basis weight of the fibers in the fibrous adhesive web, preferably 0 to 15 percent. The non-pressure-sensitive fibrous material if present solely in the form of a blend with the pressure-sensitive adhesive material is preferably from 0 to 40 percent of the basis weight of the fibers forming the adhesive-coated substrate, preferably of the substantially continuous fibers forming the adhesive-coated substrate. The use of the non-adhesive material with the pressure-sensitive adhesive material decreases adhesion, however, it can also increase breathability. Where the non-pressure-sensitive adhesive fibrous material is present as a discrete fiber, these fibers are generally intimately commingled with the pressure-sensitive adhesive fibers. If the non-pressure-sensitive fibrous component is present as commingled fibers, these fibers can be formed from the same die as per U.S. Pat. No. 5,601,851, or in a separate die which could direct the non-pressure-sensitive adhesive fibers directly, or subsequently, into the fiber stream containing the pressure-sensitive adhesive fibers prior to collection of either fiber on a collection surface. The use of multiple dies for forming commingled fibers is known in the art. Further commingled fibers could be added as discrete staple fibers as is known in the art. The adhesive layer generally has a basis weight of from 5 to 200 g/m$^2$, preferably 20 to 100 g/m$^2$, wherein preferably at least 50 percent of the adhesive layer is in the form of pressure-sensitive adhesive fibers, preferably 85 to 100 percent.

Figure 2:
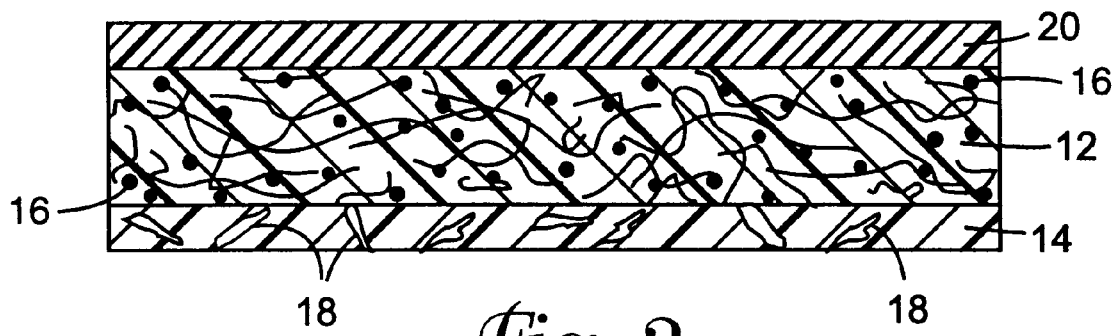
FIG. 2 is a cross-sectional view of an adhesive-coated substrate according to the present invention.

A preferred article according to the present invention is shown in FIG. 2. This shows a cross-sectional view of the article which consists of a backing substrate comprising a nonwoven web 12 containing superabsorbent particles 16 and having coated thereon a fibrous adhesive layer 14 comprising an entangled web of pressure-sensitive adhesive fibers 18. On the opposite surface of the backing substrate is an optional breathable, liquid impervious film 20.

EXAMPLES

All patents, patent applications, and publications are incorporated herein by reference in their entirety as if each were individually incorporated herein. The following examples are offered to aid in understanding of the present invention and are not to be construed as limiting the scope thereof. Unless otherwise indicated, all parts and percentages are by weight.

Test Protocols
Adhesion to Dry and Wet Skin

Evaluation of the adhesiveness of a composition to human skin is an inherently temperamental determination. Human skin possesses wide variations in composition, topography, and the presence/absence of various body fluids. However, comparative average values of tape adhesion are attainable by using test results from several individuals as described herein.

Initial skin adhesion ($T_0$) to dry or wet skin was measured in accordance with the widely accepted PSTC-1 Peel Adhesion Test (incorporated herein by reference), a testing protocol established by the Specifications and Technical Committee of the Pressure Sensitive Tape Council located at 5700 Old Orchard Road, Skokie, Ill. The test was modified for our purposes by applying the tape to the skin of a living human.

Two samples (one for wet-skin testing and one for dry-skin testing), each measuring 2.5-cm wide by 7.6-cm long, were applied to the back of each of one to two human subjects. The subjects were placed in a prone position with arms at their sides and heads turned to one side. Samples were applied without tension or pulling of skin to both sides of the spinal column with the length of each sample positioned at a right angle to the spinal column.

Those samples tested for wet skin adhesion were applied to skin which had been moistened with a water saturated cloth, leaving visually observable drops of standing water, immediately before application of the sample.

The samples were pressed into place with a 2-kg roller moved at a rate of approximately 2.5 cm/sec with a single forward and reverse pass. No manual pressure was applied to the roller during application.

The samples were then removed immediately after application ($T_0$) at a removal angle of 180° and at a removal rate of 15 cm/min using a conventional adhesion tester equipped with a 11.3 kg test line attached to a 2.5 cm clip. The clip was attached to the edge of the sample furthest from the spinal column by manually lifting about 1 cm of the sample from the skin and attaching the clip to the raised edge. The adhesion tester was a strain-gauge mounted on a motor-driven carriage.

The measured force required to effect removal of each tape sample was reported (as an average of two sample replications) in Newtons (N) per cm. Preferably, to adhere to wet skin, the ($T_0$) wet value is greater than about 0.08 N/cm and it is desired that the ($T_0$) wet value is approximately the same as the ($T_0$) dry value.

Adhesive Starting Materials
Adhesive 1 (BMF-PSA Web)

An acrylate-based blown micro fiber (BMF)-pressure sensitive adhesive (PSA) web was prepared using a melt blowing process similar to that described, for example, in Wente, Van A., "Superfine Thermoplastic Fibers," in *Industrial Engineering Chemistry*, Vol. 48, pages 1342 et seq (1956) or in Report No. 4364 of the Naval Research Laboratories, published May 25, 1954, entitled "Manufacture of Superfine Organic Fibers" by Wente, Van A.; Boone, C. D.; and Fluharty, E. L., except that the BMF apparatus utilized a single extruder which fed its extrudate to a gear pump that controlled the polymer melt flow. The gear pump fed a feedblock assembly that was connected to a melt-blowing die having circular smooth surface orifices (10/cm) with a 5:1 length to diameter ratio. The primary air was maintained at 220° C. and 241 KPa with a 0.076 cm gap width to produce a uniform web. The feedblock assembly was fed by a polymer melt stream (240° C.) comprised of isooctyl acrylate/acrylic acid/styrene macromer terpolymer (IOA/AA/Sty, 92/4/4 weight ratio, Inherent Viscosity of approximately 0.65 as measured by conventional means using a Cannon-Fenski #50 viscometer in a water bath controlled at 25° C. to measure the flow time of 10 ml of a polymer solution (0.2 g per deciliter polymer in ethyl acetate)) PSA, prepared as described in Example 2 of U.S. Pat. No. 5,648,166. Both the die and feedblock assembly were maintained at 220° C., and the die was operated at a rate of 178 g/hr/cm die width. The BMF-PSA web was collected on a double coated silicone release paper (Daubert Coated Products, Westchester, Ill.) which passed around a rotating drum collector at a collector to die distance of 17.8 cm. The resulting BMF-PSA web, comprising PSA microfibers having an average diameter of less than about 10–25 microns (as determined using a scanning electron microscope), had a basis weight of about 50 g/m².

Adhesive 2 (BMF-PSA Web)

An acrylate-based BMF-PSA web was prepared using a melt blowing process similar to that described for making Adhesive 1, except that two polymer melt streams were employed to afford microfibers comprised of the following two layers: IOA/AA/Sty macromer terpolymer (92/4/4 weight ratio) and IOA/AA/EOA [poly(Ethylene Oxide Acrylate)] terpolymer (70/15/15 ratio) in a weight ratio of 75 to 25, respectively. The resulting web had a basis weight of about 28 g/m². A more detailed description of preparing BMF-PSA webs comprised of multilayered polymeric fibers can be found in pending U.S. patent application Ser. No. 08/980,921.

Backings 1–3 (BMF-PSA Webs)

A BMF-PSA web was prepared using a melt blowing process similar to that described for making Adhesive 1, except that HL2547 block copolymer adhesive (H.B. Fuller Company, St. Paul, Minn.) was substituted for the IOA/AA/Sty macromer terpolymer. The resulting web had a basis weight of about 30 g/m² (Backing 1). Similarly, BMF-PSA webs were prepared with basis weights of 48 g/m² (Backing 2) and 50 g/m² (Backing 3).

Backing 4 (BMF-PSA Web)

A BMF-PSA web comprised of three-layer polymeric fibers was prepared using a melt blowing process similar to that described for making Example 1 of pending U.S. patent application Ser. No. 08/980,921, except that the two polymer melt streams consisted of EASTOFLEX D-127S polyalpha-olefin PSA (Eastman Chemical Co., Kingsport, Tenn.) and ESCORENE 3795 polypropylene resin (Exxon Chemicals, Houston, Tex.). The polypropylene resin contained 1.5% by weight of FC-171 fluorochemical surfactant. The gear pumps were adjusted to produce a 25/75 ratio of poly alpha olefin PSA to polypropylene resin (based on a pump ratio percent) with the outermost layers of the fibers being the adhesive. The resulting BMF-PSA web had a basis weight of about 50 g/m².

Example 1

Adhesive Tape with SAP-Containing BMF-PSA Web Backing

A BMF-PSA web backing was prepared as described for Backing 4, except that a carboxymethylcellulose superabsorbent polymer (SAP) was added during melt blowing at a level of 30 g/m$^2$. An adhesive tape was then constructed by laminating together the following three materials using a conventional laboratory laminator at room temperature:

1. TEGADERM 1626W adhesive dressing (3M Company, St. Paul, Minn.)—Top Layer (Film with adhesive side in contact with Center Layer.)
2. Backing: Backing 4 (BMF-PSA Web) containing 30 g/m$^2$ SAP—Center Layer
3. Adhesive 2 (BMF-PSA Web) intended for contact with skin—Bottom Layer A sample of the resulting adhesive tape was applied to a human subject's skin that had been wet with a spray of water. The tape adhered aggressively to the wet skin such that the absorbent web (Center Layer) delaminated internally before the adhesive tape could be peeled from the skin.

Example 2

Adhesive Tape with SAP-Containing BMF-PSA Web Backing

An adhesive tape was constructed as described in Example 1, except that Adhesive 1 was substituted for Adhesive 2 as the Bottom Layer of the construction. When applied to wet skin, this tape adhered aggressively.

Example 3

Adhesive Tape with SAP-Containing BMF-PSA Web Backing

An adhesive tape was constructed as described in Example 1, except that TRANSPORE plastic tape (3M Company) was substituted for the TEGADERM adhesive dressing as the Top Layer of the construction.

Comparative Example 1

Adhesive Tape without SAP-Containing BMF-PSA Web Backing

An adhesive tape was constructed as described in Example 1, except that the BMF-PSA backing (Center layer) of the construction was excluded. The resulting tape did not adhere to a useful level to wet skin.

Examples 4–14

Adhesive Tapes with SAP-Containing BMF-PSA Web Backings

A series of BMF-PSA web backings were prepared as described for Backings 1–3, except that different SAPs were added during melt blowing at levels of 20–87 g/m$^2$. A series of adhesive tapes were then constructed by laminating together the following materials using a conventional laboratory laminator at room temperature:

1. TEGADERM 1626W adhesive dressing (3M Company)—Top Layer (Film with adhesive side in contact with Center Layer).
2. Backing: Backing 1, 2, or 3 (BMF-PSA Web) containing SAP—Center Layer.
3. Adhesive 1 (BMF-PSA Web) intended for contact with skin—Bottom Layer.

The specific SAPs utilized and the adhesive tapes constructed are listed in Table 1.

The resulting adhesive tapes were cut into samples and evaluated for adhesion to dry and wet skin. Results are provided in Table 1.

Example 15

Adhesive Tape with SAP-Containing BMF-PSA Web Backing

An adhesive tape was constructed as described in Example 4 by laminating together the following materials using a conventional laboratory laminator at room temperature:

1. TEGADERM 1626W adhesive dressing (3M Company)—Top Layer (Film with adhesive side in contact with Center Layer.)
2. Backing: Backing 1 (BMF-PSA Web) containing AQUALON (CMC-Carboxymethylcellulose) SAP at 160 g/m$^2$—Center Layer
3. Adhesive 1 (BMF-PSA Web) intended for contact with skin—Bottom Layer The resulting adhesive tape was cut into samples and evaluated for adhesion to dry and wet skin. Results are provided in Table 2.

Example 16

Adhesive Tape with SAP-Containing BMF-PSA Web Backing

An adhesive tape was constructed as described in Example 15, except that the TEGADERM 1626W Top layer was replaced by a woven cellulose acetate-taffeta web coated with a PSA as described in U.S. Pat. No. 4,693,776. The latter adhesive-coated web closely resembled commercial DURAPORE surgical tape (3M Company). The resulting adhesive tape was cut into samples and evaluated for adhesion to dry and wet skin. Results are provided in Table 2.

Example 17

Adhesive Tape with SAP-Containing BMF-PSA Web Backing

An adhesive tape was constructed as described in Example 15, except that the TEGADERM 1626W Top Layer was replaced by an extruded polyethylene film (3-mil in thickness) coated with a PSA as described in U.S. Pat. No. 4,693,776. The resulting adhesive tape was cut into samples and evaluated for adhesion to dry and wet skin. Results are provided in Table 2.

Example 18

Adhesive Tape with SAP-Containing BMF-PSA Web Backing

An adhesive tape was constructed as described in Example 15, except that, during melt blowing of Backing 1, AQUALON (CMC) was added at a level of 30 g/m$^2$ and carbon black was additionally added at a level of 70 g/m$^2$. The resulting adhesive tape was cut into samples and evaluated for adhesion to dry and wet skin. Results are provided in Table 2.

Comparative Example 2

Adhesive Tape without SAP-Containing BMF-PSA Web Backing

An adhesive tape was constructed as described in Example 16, except that the BMF-PSA backing (Center Layer) of the construction was excluded. The resulting adhesive tape was cut into samples and evaluated for adhesion to dry and wet skin. Results are provided in Table 2.

Comparative Example 3

Adhesive Tape without SAP-Containing BMF-PSA Web Backing

An adhesive tape was constructed as described in Example 17, except that the BMF-PSA backing (Center Layer) of the construction was excluded. The resulting adhesive tape was cut into samples and evaluated for adhesion to dry and wet skin. Results are provided in Table 2.

Example 19

Adhesive Tape with SAP-Containing BMF-PSA Web Backing

An adhesive tape was constructed as described in Example 9, except that a conventional tackified block copolymer based on KRATON 1119 (Shell Chemical Company, Houston, Tex.) applied as coated stripes at about 6 stripes/cm (approximately 40% of surface covered by adhesive) was used in place of Adhesive 1 as the Bottom Layer. The resulting adhesive tape was cut into samples and evaluated for adhesion to dry and wet skin. Results are provided in Table 3.

Example 20

Adhesive Tape with SAP Fibers

A nonwoven carrier web comprised of 80% poly(ethylene terephthalate) PET T295 fibers (6 denier, 3.8-cm long, Hoechst-Celanese Corporation, Charlotte, N.C.) and 20% SAP OASIS fibers (52-mm long, 0.03-mm diameter, Technical Absorbents Limited, Ontario, Canada) was prepared on Rando Webber carding equipment and needle-tacked at 250 strokes/min. The carrier web had a final basis weight of 150 g/m$^2$.

The carrier web was then fed through a macro-dropper that separated the fibers and dropped them into a stream of melt-blown polyurethane fibers such that the fibers were incorporated into the resulting BMF web. The melt-blown web was prepared from Morton MORTHANE PS440-200 polyurethane (Morton International, Seabrook, N.H.) as described in Example 1 of U.S. Pat. No. 5,230,701. The final nonwoven web backing was comprised of 75% polyurethane and 25% carrier web.

An adhesive tape was then constructed as described in Example 1, except that Adhesive 1 was substituted for Adhesive 2 as the Bottom Layer of the construction. The resulting tape was found to adhere aggressively when applied to either wet or dry skin. Quantitative measurement of adhesion according to the test method described herein was not possible as the web backing delaminated internally before the adhesive bond to skin failed.

Example 21

Adhesive Tape with SAP Fibers

An adhesive tape was constructed as described in Example 20, except that the composition of the final web backing was 50% polyurethane and 50% carrier web. The resulting tape was found to adhere aggressively when applied to either wet or dry skin. Quantitative measurement of adhesion according to the test method described herein was not possible as the web backing delaminated internally before the adhesive bond to skin failed.

Example 22

Adhesive Tape with SAP Fibers

An adhesive tape was constructed as described in Example 21, except that the composition of the nonwoven carrier web was 50% PET T295 fibers and 50% OASIS SAP fibers with a final basis weight of 165 g/m$^2$. The resulting tape was found to adhere aggressively when applied to either wet or dry skin. Quantitative measurement of adhesion according to the test method described herein was not possible as the web backing delaminated internally before the adhesive bond to skin failed.

Example 23

Adhesive Tape with SAP Fibers

An adhesive tape was constructed as described in Example 22, except that the composition of the final web backing was 75% polyurethane and 25% carrier web. The resulting tape was found to adhere aggressively when applied to either wet or dry skin. Quantitative measurement of adhesion according to the test method described herein was not possible as the web backing delaminated internally before the adhesive bond to skin failed.

Example 24

Adhesive Tape with SAP Fibers

An adhesive tape was constructed as described in Example 22, except that the composition of the final web backing was 90% polyurethane and 10% carrier web. The resulting tape was found to adhere aggressively when applied to either wet or dry skin. Quantitative measurement of adhesion according to the test method described herein was not possible as the web backing delaminated internally before the adhesive bond to skin failed.

The adhesive tapes described in Examples 20–24 would be expected to have greater internal cohesive strength if laminated under conditions of greater pressure and/or temperature.

Evaluations

Adherence to Dry and Wet Skin Results

Adhesive tape samples from Examples 1–3 and Comparative Example 1 were qualitatively evaluated for adherence to wet skin. Samples constructed with a BMF-PSA backing containing 30 g/m$^2$ SAP and utilizing a BMF-PSA skin adhesive (Examples 1–3) adhered aggressively to wet skin, whereas a similar adhesive construction without the SAP-containing BMF-PSA backing (Comparative Example 1) did not adhere to a useful level to wet skin.

Adhesive tape samples from Examples 4–14 were quantitatively evaluated for adherence to dry and wet skin (see Test Procedures) with the results provided in Table 1. These results demonstrate that adhesive tapes constructed with a porous skin adhesive (BMF-PSA web), a BMF-PSA web backing containing sufficient levels of a SAP, and a thin film (e.g., TEGADERM dressing) top layer, had good to excellent wet skin adhesion.

Adhesive tape samples from Examples 15–18 and Comparative Examples 2–3 were quantitatively evaluated for adherence to dry and wet skin with the results provided in Table 2. These results demonstrate that adhesive tapes constructed with a porous skin adhesive (BMF-PSA web), a BMF-PSA web backing containing sufficient levels of a SAP, and a thin film (e.g., TEGADERM dressing, Ex. 15) or absorbent (e.g., woven acetate-taffeta, Ex. 16) Top Layer, had good to excellent wet skin adhesion. Control Example 2 (C2) also had good wet skin adhesion that would be expected from a tape having a porous adhesive and a water absorbent backing. The adhesive tapes of Examples 15, 16, and C2 also possessed the desirable feature of having wet skin and dry skin adhesions nearly equal. The adhesive tapes of Examples 17 and C3 were constructed with a polyethylene top layer that was not water absorbent and that resulted in a somewhat stiff construction. These factors apparently contributed to the relatively lower wet skin adhesion results that were obtained. Results from testing the commercial products, DURAPORE Dressing (3M Company) and BLENDERM Surgical Tape (3M Company) are also shown in Table 2. Both of these products showed significantly greater adhesion to dry skin than to wet skin.

The adhesive tape samples from Example 19 were quantitatively evaluated for adherence to dry and wet skin with the results provided in Table 3. These results demonstrated that an adhesive tape constructed with a porous skin adhesive (e.g., a discontinuous adhesive achieved by applying a tackified KRATON polymer in a striped pattern), a BMF-PSA web backing containing sufficient levels of a SAP, and a thin film (e.g., TEGADERM dressing) Top Layer had good wet skin adhesion. The adhesive tape of Example 19 also possessed the desirable feature of having wet skin and dry skin adhesions nearly equal.

It is concluded from these examples that adhesive tapes having a porous skin adhesive and an absorbent, SAP-containing backing can be constructed to possess practically useful levels of wet skin adhesion, especially as compared to the wet skin adhesion of commercially available adhesive tapes.

TABLE 1

Tape Samples - Adhesion to Dry and Wet Skin
[Top Layer = TEGADERM 1626W; Bottom Layer = Acrylate-Based BMF-PSA (Adhesive 1)]

| Ex. | BMF-PSA Web (Basis Wt. g/m$^2$) | Superabsorbent Polymer (Loading Weight, g/m$^2$) | No. of Subjects | Samples/ Subject | Initial Skin Adhesion ($T_o$) Dry (N/cm) | Wet (N/cm) |
|---|---|---|---|---|---|---|
| 4 | Backing 1 (30) | AQUALON Sodium CMC (20) Carboxymethyl-cellulose (Hercules, Inc, Wilmington, DE) | 1 | 2 | 0.22 | 0.16 |
| 5 | Backing 1 (30) | AQUALON Sodium CMC (30) | 1 | 2 | 0.24 | 0.17 |
| 6 | Backing 1 (30) | AQUALON Sodium CMC (45) | 1 | 2 | 0.21 | 0.19 |
| 7 | Backing 1 (30) | NORSOCRYL S-35 (27) Sodium Polyacrylate (100–800 μm) (ELF Altochem Polymers Division, Philadelphia, PA) | 1 | 2 | 0.29 | 0.27 |
| 8 | Backing 1 (30) | NORSOCRYL S-35 (21) | 1 | 2 | 0.33 | 0.24 |
| 9 | Backing 1 (30) | NORSOCRYL S-35 (45) | 1 | 2 | 0.33 | 0.28 |
| 10 | Backing 2 (48) | AP 80 HS (24) Sodium Polyacrylate (1–100 μm) (Stockhausen, Inc, Greensboro, NC) | 1 | 2 | 0.32 | 0.18 |
| 11 | Backing 2 (48) | AP 80 HS (24) | 1 | 2 | 0.27 | 0.20 |
| 12 | Backing 3 (50) | AP 80 HS (24) | 1 | 2 | 0.27 | 0.16 |
| 13 | Backing 3 (50) | AQ + 12% PEMULEN TR-1 (22) PEMULEN Polymeric Emulsifier (B. F. Goodrich, Cleveland, OH) | 1 | 2 | 0.30 | 0.16 |
| 14 | Backing 3 (50) | AQ + 12% PEMULEN TR-1 (46) | 1 | 2 | 0.25 | 0.16 |

TABLE 2

Tape Samples - Adhesion to Dry and Wet Skin
[Bottom Layer = Acrylate-Based BMF-PSA (Adhesive 1)]

| Ex. | Top Layer | BMF-PSA Web (g/m$^2$) SAP (Loading Wt, g/m$^2$) | No. of Subjects | Samples/ Subject | Initial Skin Adhesion ($T_o$) Dry (N/cm) | Wet (N/cm) |
|---|---|---|---|---|---|---|
| 15 | TEGADERM | Backing 1 (30) AQUALON (160) | 2 | 2 | 0.30 | 0.30 |
| 16 | Woven Cellulose Acetate-Taffeta + PSA | Backing 1 (30) AQUALON (160) | 2 | 2 | 0.22 | 0.19 |
| 17 | Polyethylene Film + PSA | Backing 1 (30) AQUALON (160) | 2 | 2 | 0.23 | 0.13 |
| 18 | TEGADERM | Backing 1 (30) AQUALON (30) Carbon Black (70) | 2 | 2 | 0.28 | 0.20 |
| C2 | Woven Cellulose Acetate-Taffeta | None | 2 | 2 | 0.24 | 0.23 |
| C3 | Polyethylene Film | None | 2 | 2 | 0.25 | 0.13 |
| | DURAPORE Dressing (3M) | None | 1 | 2 | 0.46 | 0.25 |
| | BLENDERM | None | 1 | 2 | 0.56 | 0.14 |

TABLE 2-continued

Tape Samples - Adhesion to Dry and Wet Skin
[Bottom Layer = Acrylate-Based BMF-PSA (Adhesive 1)]

| Ex. | Top Layer | BMF-PSA Web (g/m²) SAP (Loading Wt, g/m²) | No. of Subjects | Samples/ Subject | Initial Skin Adhesion (T₀) Dry (N/cm) | Wet (N/cm) |
|---|---|---|---|---|---|---|
| | Surgical Tape (3M) | | | | | |

TABLE 3

Tape Samples - Adhesion to Dry and Wet Skin
[Top Layer = TEGADERM ™ 1626W;
Bottom Layer = Tackified KRATON ™ (striped)]

| Ex. | BMF-PSA Web (Basis Wt. g/m²) | Superabsorbent Polymer (Loading Weight, g/m²) | No. of Subjects | Samples/ Subject | Initial Skin Adhesion (T₀) Dry (N/cm) | Wet (N/cm) |
|---|---|---|---|---|---|---|
| 19 | Backing 1 (30) | NORSOCRYL S-35 (45) | 1 | 2 | 0.21 | 0.20 |

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

We claim:

1. An article comprising a backing substrate and a discontinuous adhesive layer disposed thereon, wherein the backing substrate comprises a fibrous web and absorbent particulate material, and further wherein the article has an initial wet skin adhesion of at least about 20 g/2.5 cm (0.08 N/cm).

2. The article of claim 1 wherein the initial dry skin adhesion is at least about 20 g/2.5 cm (0.08 N/cm).

3. The article of claim 2 wherein the initial wet skin adhesion is at least about 65% of the initial dry skin adhesion.

4. The article of claim 3 wherein the initial wet skin adhesion is about 65% to about 135% of the initial dry skin adhesion.

5. The article of claim 1 wherein the absorbent particulate material has a length to width ratio of no more than about 20:1.

6. The article of claim 1 wherein the absorbent particulate material has a length to width ratio of greater than about 100:1.

7. The article of claim 1 wherein the absorbent particulate material has a particle size of less than about 800 microns.

8. The article of claim 1 wherein the absorbent particulate material is distributed uniformly throughout the fibrous web of the backing substrate.

9. The article of claim 1 wherein the absorbent particulate material is disposed onto a major surface of the fibrous web of the backing substrate.

10. The article of claim 1 wherein the absorbent particulate material is capable of absorbing at least about 50 times its weight in water.

11. The article of claim 1 wherein the absorbent particulate material is prepared from carboxymethylcellulose, hydroxymethylcellulose, hydroxyethylcellulose, poly (acrylamide), poly(acrylic acid), alginates, starch-graft copolymers, or their sodium or potassium salts.

12. The article of claim 1 wherein the absorbent particulate material is prepared from gelatins, polysaccharides, or gums.

13. The article of claim 1 wherein the fibrous web of the backing substrate comprises pressure-sensitive adhesive fibers.

14. The article of claim 1 wherein the fibrous web of the backing substrate comprises multilayer fibers.

15. The article of claim 1 wherein the backing substrate comprises a laminate that includes a breathable, liquid impervious film.

16. The article of claim 15 wherein the backing substrate laminate includes a fibrous web without particulate material.

17. The article of claim 1 wherein the initial wet skin and dry skin adhesion is at least about 40 g/2.5 cm (0.08 N/cm).

18. The article of claim 1 wherein the discontinuous adhesive layer comprises pressure-sensitive adhesive fibers.

19. The article of claim 18 wherein the pressure-sensitive adhesive fibers are commingled with non-pressure-sensitive adhesive fibers.

20. The article of claim 1 which is in the form of a wound dressing.

21. An article comprising a backing substrate and a discontinuous adhesive layer disposed thereon, wherein the backing substrate comprises a fibrous web and absorbent particulate material, the discontinuous adhesive layer comprises pressure-sensitive adhesive fibers, and further wherein the article has an initial wet skin adhesion of at least about 20 g/2.5 cm (0.08 N/cm) which is at least about 65% of the initial dry skin adhesion.

22. A method of making an adhesive article, the method comprising providing a backing substrate and applying a discontinuous adhesive layer to a major surface thereof, wherein the backing substrate comprises a fibrous web and absorbent particulate material, and further wherein the article has an initial wet skin adhesion of at least 20 g/2.5 cm (0.08 N/cm).

23. A method of using an adhesive article, the method comprising:

providing an adhesive article comprising a backing substrate and a discontinuous adhesive layer disposed thereon, wherein the backing substrate comprises a fibrous web and absorbent particulate material, and further wherein the article has an initial wet skin adhesion of at least 20 g/2.5 cm (0.08 N/cm); and adhering the adhesive article to skin.

* * * * *